United States Patent [19]
Guering et al.

[11] Patent Number: 5,694,479
[45] Date of Patent: Dec. 2, 1997

[54] PROCESS FOR MEASURING THE OPTICAL QUALITY OF A GLASS PRODUCT

[75] Inventors: Paul-Henri Guering, Paris; Patrick Gayout, Gagny; Jean-Michel Florentin, Compiegne; Michel Pichon, Gouvieux, all of France

[73] Assignee: Saint Gobain Vitrage, Courbevoie, France

[21] Appl. No.: 458,823

[22] Filed: Jun. 2, 1995

[30] Foreign Application Priority Data

Jun. 2, 1994 [FR] France ........................... 94-06774

[51] Int. Cl.⁶ ........................................ G01N 21/88
[52] U.S. Cl. .................... 382/141; 348/92; 348/130; 356/239; 356/392
[58] Field of Search ........................ 356/239, 240, 356/433, 432, 371, 376, 391, 392, 394, 436, 445, 448; 382/141, 142, 279; 65/378; 348/92, 127, 129, 130; 364/468.16, 468.17

[56] References Cited

U.S. PATENT DOCUMENTS

| | | | |
|---|---|---|---|
| 4,647,197 | 3/1987 | Kitaya et al. | 356/239 |
| 4,930,889 | 6/1990 | Van Donselaar et al. | 356/237 |
| 5,363,188 | 11/1994 | Didelot et al. | 356/124.5 |

*Primary Examiner*—Leo Boudreau
*Assistant Examiner*—Brian P. Werner
*Attorney, Agent, or Firm*—Oblon, Spivak, McClelland, Maier & Neustadt, P.C.

[57] ABSTRACT

For evaluating the optical quality of a glass product utilizing a projection technique, a camera and a computer, the image observed is compared with a reference image reconstructed by means of a convolution window which is displaced over the entire projected image. The illumination at the boundaries is reconstructed by an extrapolation by two-dimensional linear regression.

7 Claims, 3 Drawing Sheets

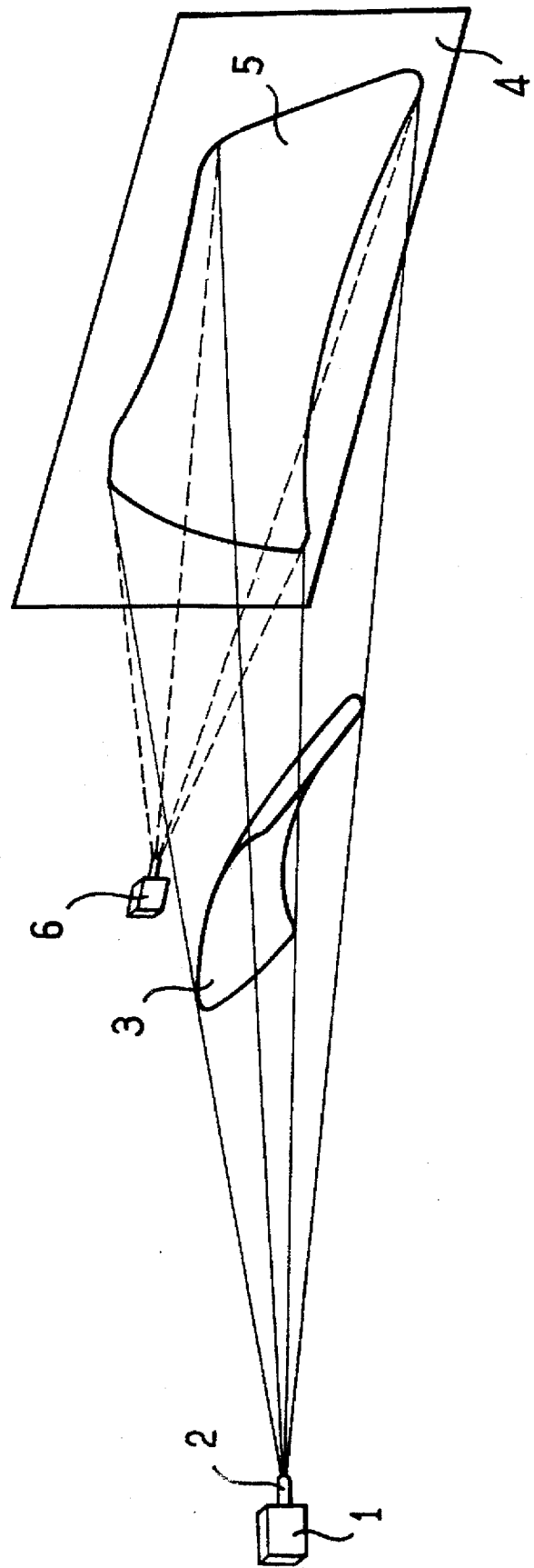
FIG_1

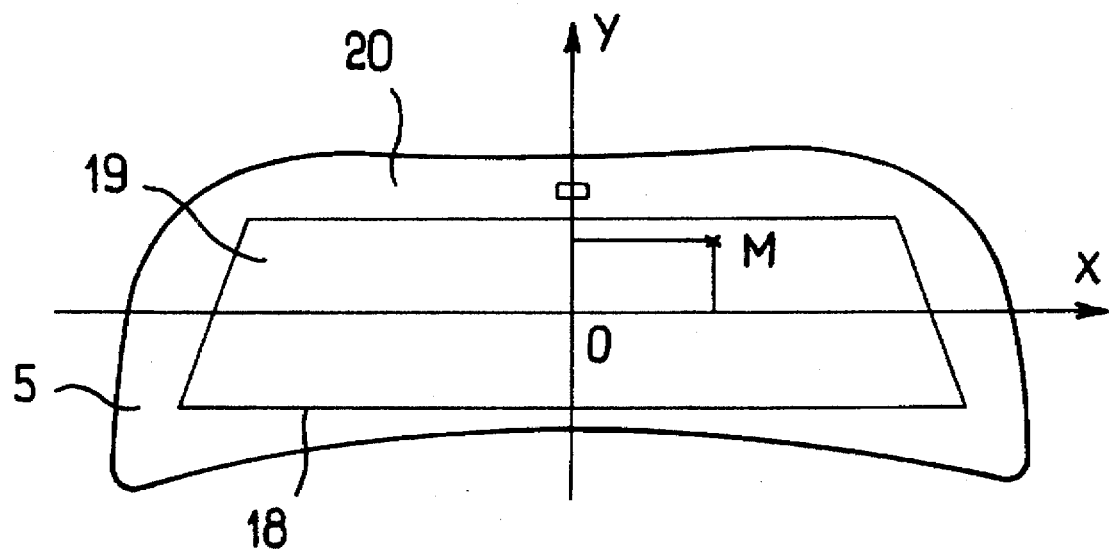
FIG_2
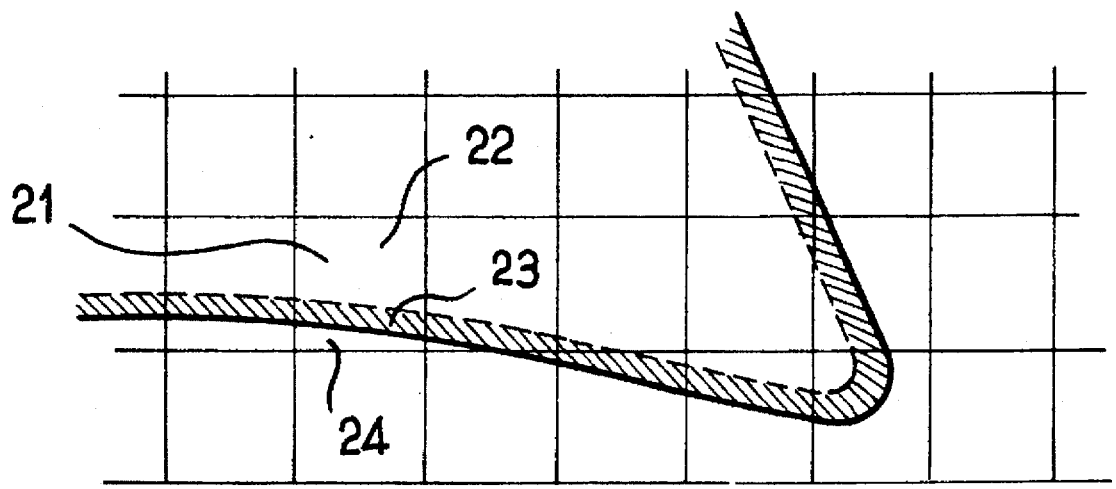
FIG_3

PROCESS FOR MEASURING THE OPTICAL QUALITY OF A GLASS PRODUCT

FIELD OF THE INVENTION

The invention is related to techniques for measuring the optical defects of glass products, and particularly of glass products for motor vehicles.

DESCRIPTION OF THE RELATED ART

In a general way, industry is seeking more and more to control the quality of the products which is manufactures. This is true, in particular, of the optical quality of glass products. In order to achieve this object, all the parameters of the production are maintained within very narrow ranges. It is nevertheless possible that an incident of production parameters going outside the permitted ranges may occur. Moreover, if such an incident occurs, its effect on product quality is not always known. Therefore, examination of the quality on 100% of the production continues to be essential in numerous cases.

With regard to glass products, there is frequently a need to continuously evaluate the optical quality thereof. It may, in particular, be desired to select the flat glass emerging from production lines in order to allocate it for a particular use such as for example a mirror intended for scientific applications or a thin flat glass intended to be transformed into a very sloping windscreen. In a general way, moreover, the windscreens of modern motor vehicles are particularly monitored with regard to their optical quality. This criterion affects the problem of safety in driving motor vehicles. The shapes of the windscreens, their slope, the materials from which they are manufactured—very thin glasses or even transparent polymers—necessitate a very careful control of the optical quality, it frequently being necessary to carry out such evaluation of 100% of the products being produced.

Ombroscopic methods for evaluating the optical quality of glass products have long been known and used. They are frequently associated with CCD cameras which permit an illumination measurement to be obtained at each point of a screen illuminated by a localized light source, the rays of which pass through the glass product before reaching the screen. The analysis of the image is then undertaken using a computer.

In U.S. Pat. No. 5,016,099, panels of float glass of large dimensions are measured by illuminating a moving horizontal strip using grazing light and by observing, through the glass, the shadow projected onto a screen which is close to the glass and parallel to it. A CCD camera measures a band perpendicular to the direction of movement and compares the illumination at a point with a reference illumination, i.e., that which would exist at the same point if the sheet of glass were plane, with parallel faces and free from defects. A variant of the process provides for utilizing as a reference illumination the illumination of the screen at the point of measurement, but where all illumination variations exceeding a certain spatial frequency have been eliminated (low-pass filtering). In addition to the fact that this method performs the measurement only in a single direction, said method presents a problem where the boundaries of the plate are approached, since then the reference measurement becomes a asymmetric; this falsifies the measurement.

In U.S. Pat. No. 5,146,282, a method is proposed for the ombroscopic measurement of a glass product such in a glass product for motor vehicles. The present invention is an improvement of the method described in this document and consisting of comparing the illumination at a point with the illumination at the same point in the absence of glass products, said reference illumination being weighted as a function of the optical and geometric characteristics of the corresponding point on the glass product.

The technique of U.S. Pat. No. 5,146,282, permits an easy and precise measurement. Unfortunately, the calibration procedure, in the course of which a precise measurement of the optical and geometric characteristics of each point of the glass product must be performed, is lengthy and delicate.

SUMMARY OF THE INVENTION

It is an object of the present invention to improve the aforementioned two processes. In contrast to the first process, this involves permitting a measurement of the defects irrespective of what may be their orientation and enabling a precise measurement as far as the boundaries of the plate. As compared with the process of U.S. Pat. No. 5,146,282, this involves avoiding the calibration procedure and guaranteeing a precise measurement under the most widely varying conditions and, in particular, irrespective of what may be the inclination and the luminous transmittance of the glass products.

The invention provides a process for measuring the optical quality in the measurement surface of a glass product in which it is illuminated using a localized light source, wherein the ombroscopic image obtained is recorded on a screen, wherein point measurements are made of the illumination and wherein the illumination of a point of the image is compared with the reference illumination corresponding to a glass product free from defects and in which the reference illumination is the same as the weighted illumination of a convolution window, the measurement point of which is the center. This illumination is obtained by the computation of the weighted average of the point measurements made or estimated on all the measurement points of the window.

Where the convolution window of the image includes regions in which the direct measurement of the illumination is impossible or prohibited, the values measured in these regions are replaced by estimated values which are extrapolated from those measured in the surfaces adjacent to the regions excluded from the measurement.

The estimation of the illuminations in the excluded regions in undertaken by the following steps. First, a grid is superimposed on the measurement surface of the glass products. The boundary grids of the excluded regions are then identified. The average illumination of the enabled part of the boundary grid and the percentage of the surface area of this part of the grid are then calculated. The average illumination of the prohibited part of the boundary grid is then calculated by extrapolation from the adjacent grids and from the enabled part of said boundary grid, each weighted as a function of its surface not excluded from the measurement.

After having estimated the illuminations in the excluded regions, a complete reference image is reconstructed by carrying out a convolution filtering on the selected window, the center of which in displaced over the entire measurement surface.

This complete reference image is held in memory to serve for comparison with the measurement image of the same glass product or, subsequently, for comparison with the measurement image of another glass product of the same series.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 1 shows the arrangement of elements for measuring a glass product

FIG. 2 shows a glass product together with the contour of the measurement surface;

FIG. 3 shows the grid superimposed on the surface of the ombroscopic image; and

DETAILED DESCRIPTION OF THE PREFERRED EMBODIMENT

Figure 4:
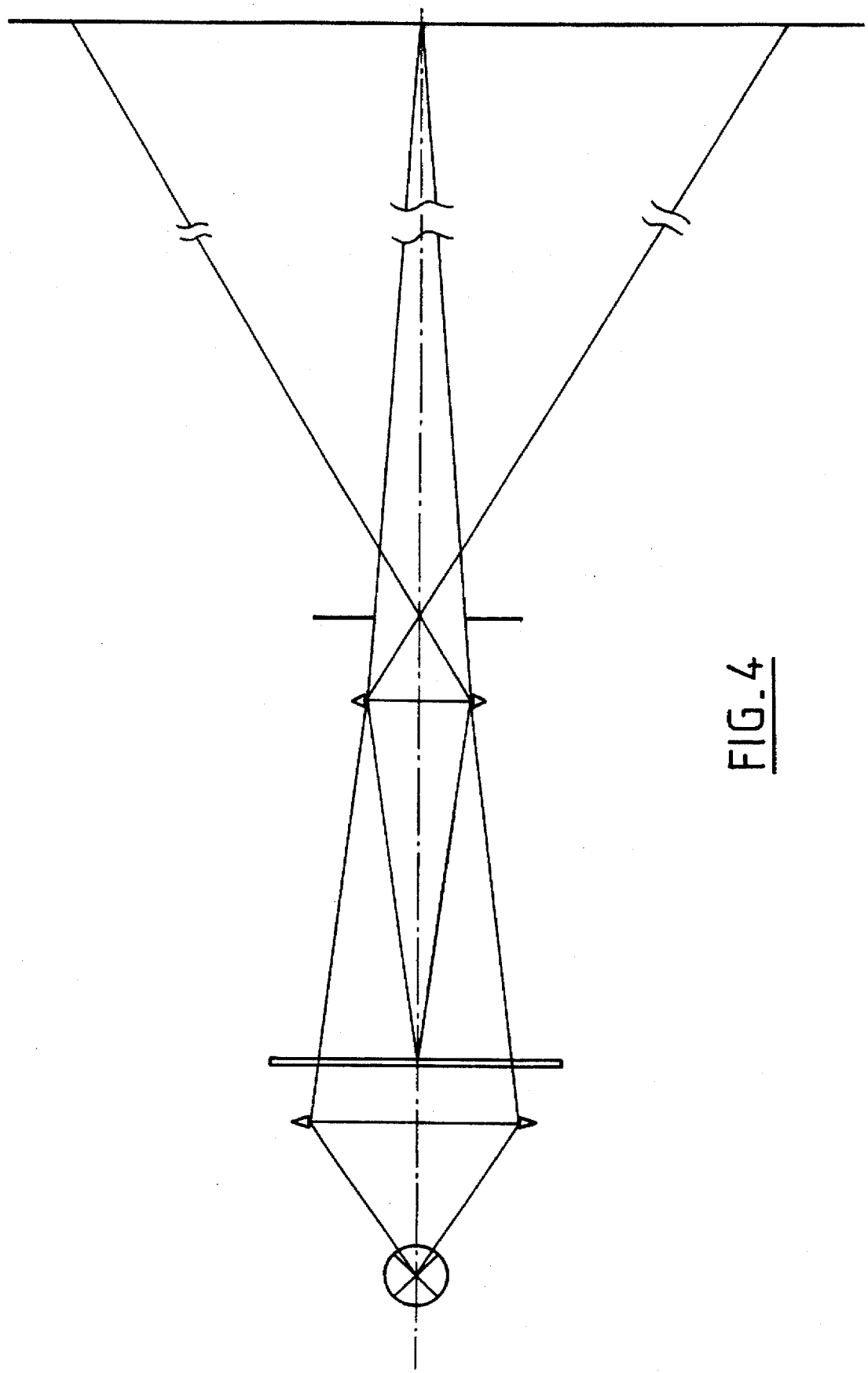
FIG. 4 is an optical diagram of the projector.

The invention utilizes the customary ombroscopic technique which consists of illuminating a glass product using a projector and observing the shadow thereof on a screen.

FIG. 1 shows the projector 1 which, by virtue of a diaphragm not shown in the Figure, acts as a point source 2. The light emerging from source 2 illuminates the glass product 3 (in the Figure, a windscreen) placed at a large distance (for example 4 meters) from the light source 2. The glass product 3 is placed under the conditions for which it is desired to detect the effect produced by the optical-power defect. It is known that for a given geometric structure of the defect of the glass, the action of the defect on vision, that in to say the optical effect of the structural defect of the glass product, is greatly dependent on the conditions of observation such as relative distances of the observer, of the glass product and of the object, but especially the angle of incidence.

In the case of windscreens, in order to have an idea of the visual effect on the driver, it is necessary to carry out the observation under real conditions. For this reason, in general, in the ombroscopic observation device, the windscreen is sloping as on the car and the optical axis of the projector is horizontal and parallel to the axis of the vehicle.

In front of the windscreen at a distance which is, for example, 4 meters, there in situated a vertical screen 4 on which the ombroscopic image 5 of the windscreen 3 is projected.

FIG. 1 further shows a video camera 6 which permits the observation of the entire shadow of the windscreen. This comprises a CCD matrix camera, for example the model 4712 from COHU Inc. (San Diego, Calif. , U.S.A.). This camera, which is able to operate at low illuminations of 0.2 lux, has 699 horizontal lines to 580 vertical lines. Under the customary conditions, a surface of 2×2 mm on the screen 4 provides one measurement point for the camera.

The siting of the camera is not critical. It is sufficient that it permits one to obtain a non-distorted view of the entire windscreen. The camera may, for example, advantageously be placed just above the windscreen, vertically to the optical axis of the projector, as shown in FIG. 1.

The shadow 5 of the windscreen 3 on the screen 4 is shown in FIG. 2. A frame 18 delimits two zones in the windscreen, a main-vision zone 19 and a peripheral zone 20. This separation into zones may correspond to a published standard (R 43 of the ECE, for example) or to specifications supplied by the constructor. In either case, the limits of the values of the optical defects to be respected in each zone are not the same.

The boundaries of the central measurement zone are either a substantive mask as in the Figure, or a digital mask, the coordinates of which are set in the memory of the computer associated with the measuring device, or the boundary established by the edge of an opaque enamelled zone.

The process of measurement is the following:

At the instant when the glass product arrives within the field of the projector, the CCD camera captures an image of the shadow of the glass product. This image is placed in memory for two purposes: for comparison with the reference image and to process the latter.

The comparison between the recorded image and the reference image will be carried out point by point by computing the ratio of the illuminations of the points of the recorded image to those of the reference image; a map of the defects will be extracted therefrom. By comparing the illumination of each defect zone with a reference level, one can measure the defect in terms of positive power (converging lens, bright zone) or negative power (diverging lens, dark zone) by the same methods as those of EP-A-0 463 940.

The processing of the reference image does not present difficulties in the central part of the glass product, where there is a continuity of the regions to be measured. The situation is different where the measurement zone stops, at the periphery of the glass product or where there are shadows on the projected image: for example on a windscreen, where a rectangle of enamel conceals the base of the rear-view mirror attached by adhesive. In these zones, it is not possible to carry out a scanning of the image by displacing thereon a window, the point of which to be measured constitutes the center and the illumination of which (weighted, average, etc . . . ) constitutes the reference. This is because where the scanning window of any shape, for example rectangular or circular, touches and especially goes beyond the boundary of a zone which is either impossible (black) or prohibited (zone not to be measured or indeed where the limit for the optical value is different), it would be necessary to prevent the fraction excluded from the window from playing a part in the computation of the reference illumination. In these circumstances, the reference illumination would not be representative and the measurement would run the risk of being approximate at the boundary limits of the measurement zones.

The method of the invention instead has the following principle: a reference image is reconstructed, which image is continuous and no longer has any boundary limits.

To do this, the dark zones are replaced by zones in which the illumination is that which logically should prevail there if the dark areas did not exist. At the exterior boundaries of the measurement zone, an illumination is artificially recreated, which is in continuity with that in the surroundings of these exterior boundaries. Thus, one either interpolates or extrapolates from the known illuminations.

The first step consists in establishing the boundaries of the enabled zone. The boundary limit may be represented in substantive form on the glass product itself: by black enamelled edging or a template placed on the glass product to separate two zones where the limits to be respected are different (zones of main and secondary vision). But most frequently it is the data processing system which "knows" the boundary limit by reference to the exterior form of the shadow on the screen. In the case of enamelled edges or the dark spots, the sudden variations of illumination caused thereby are detected.

The second step is superimposing a grid on the zones involved (FIG. 3). The grids are, for example, squares of 10×10 cm on the screen. All the boundary grids are similar to the grid 21 in FIG. 3. FIG. 3 shows three zones: a zone 22 to be measured, a black band 23 and an exterior zone 24.

An average illumination will be reconstructed in the entire grid 21. This will be composed of the illumination measured in the part 22, weighted by its surface relative to the entirety of the grid, and of a uniform illumination reconstructed for the entirety of the zones 23 and 24, also being weighted by the relative surface of the entirety of the two zones to the entirety of the grid. This illumination to be allocated to the zones 23 and 24 is the extrapolation, by two-dimensional linear regression, of the illuminations of the adjacent grid squares.

A simple geometric representation of the aforegoing operation consists in envisaging a conventional system of axes ox, oy and oz, the first two being orthogonal and horizontal, and the third vertical. On the plane xOy, there is traced a grid of squares. At the center of each grid, a vertical straight line extends to a height which is proportional to the average illumination of the grid. The two-dimensional linear regression consists in causing an average plane to pass between all these points. It will meet the vertical straight line placed at the center of the grid to be determined at a height which provides the value of the average illumination sought. The aforegoing operation produces a grid of the ombroscopic image which extends on at least one grid at the exterior of the periphery of the glass product.

The following step consists in "smoothing" the aforegoing representation. A convolution window is now displaced over the entire surface. This may have the same afore as the aforegoing grids or any shape whatsoever, but it has a surface at most equal to that of the grids. At the center of the window is the point where it is desired to know the definitive reference illumination; this is computed by a two-dimensional convolution filter. This may be a Gaussian function or, more simply, a weighted arithmetic mean of the illuminations actually measured or evaluated.

It is this third reconstructed image which will be compared with the first recorded image. The comparison consists in a division, point by point, of the illuminations:

$$\frac{Eo(x, y)}{E(x, y)}$$

In order to be carried out rapidly, it makes use of "look up tables" (L.U.T.) which permit—in real time—computation of the logarithms, subtraction thereof and computation of the exponential.

To carry out a quality measurement, it is necessary to operate within restricted ranges of illumination, where the measurement systems are linear. Two accessories are provided for the purpose of achieving this result: a special projector and a continuously variable diaphragm in front of the CCD camera.

The projector in shown in FIG. 4. Its essential feature is that of having an objective made from a single optical element (a doublet of focal length 100 mm). By making use of a MELLES GRIOT condenser having a focal length of 75 mm, this permits the formation of the image of the filament of the 250-watt quartz-iodine lamp precisely at the location of the diaphragm. This image fulfills the function of a point source of illumination. This provides a very homogeneous illumination which cannot be obtained using a conventional projector. Thus, on one and the name ombroscopic image the camera operates on a reduced range of illuminations.

To compensate for the luminosity variations due to the glass product itself (tinted glass, slope), the CCD camera was equipped with an iris diaphragm which, for each new measurement, adjusts the level of illumination within the camera to the same value.

Obviously, numerous modifications and variations of the present invention are possible in light of the above teachings. It is therefore to be understood that the invention may be practiced otherwise than as specifically described herein.

What is claimed as new and is desired to be secured by Letters Patent of the United States is:

1. A process for measuring the optical quality of a glass product, comprising the steps of:

illuminating the glass product using a localized light source to produce an ombroscopic image;

recording the ombroscopic image on a video camera;

processing point measurements of the illumination of the recorded image to reconstruct an estimated illumination in impossible or prohibited regions of the recorded image corresponding to obscured and peripheral regions of the glass product;

displacing a convolution window over the processed image;

using a two dimensional convolution filter to replace each point of the processed image with a weighted illumination at the center of the convolution window to produce a reference image corresponding to a glass product free from defects; and comparing the illumination of each point of the recorded image with corresponding points of the reference image to determine a defect in the glass product.

2. Process according to claim 1, wherein the weighted illumination comprises a computation of a weighted average of point measurements made or estimated on all the measurement points of the processed image.

3. Process according to claim 2, wherein the processing step includes the steps of estimating illumination values in said regions in which direct measurement of the illumination is impossible or prohibited, said estimated values being extrapolated from measured illumination values for surfaces adjacent to the regions in which direct measurement of the illumination is impossible or prohibited and replacing the measured values with said estimated values.

4. Process according to claim 3, wherein said step of estimating illumination values in said regions in which direct measurement of the illumination is impossible or prohibited comprises:

dividing the measurement surface of the glass product into grids, identifying boundary grids in said regions in which direct measurement of the illumination is impossible or prohibited, computing an average illumination of regions of the boundary grids in which direct measurement of the illumination is enabled, and of a percentage of the surface area of the enabled part of the grid, computing an average illumination of the boundary grids by extrapolation from adjacent grids and from the enabled part of said boundary grid, each weighted as a function of a proportion thereof of the grids.

5. Process according to claim 4, including the step of reconstructing a complete reference image by carrying out a convolution filtering on the selected window, the center of which is displaced over the entire measurement surface.

6. Process according to claim 5, including the step of holding the complete reference image in memory to serve for comparison with a measurement image of the same glass product or, subsequently, for comparison with the measurement image of another glass product of same series.

7. Process according to claim 5, including the step of holding the complete reference image in memory to serve for comparison with a measurement image of another glass product.

\* \* \* \* \*